(12) United States Patent
Ruwwe et al.

(10) Patent No.: US 7,847,133 B2
(45) Date of Patent: Dec. 7, 2010

(54) PROCESS FOR PREPARING ALKALI METAL ALKOXIDES

(75) Inventors: Johannes Ruwwe, Niederkassel (DE); Kai-Martin Krüger, Essen (DE); Udo Knippenberg, Marl (DE); Volker Brehme, Nottuln-Appelhülsen (DE); Manfred Neumann, Marl (DE)

(73) Assignee: Evonik Degussa GmbH, Essen (DE)

( * ) Notice: Subject to any disclaimer, the term of this patent is extended or adjusted under 35 U.S.C. 154(b) by 371 days.

(21) Appl. No.: 12/153,888

(22) Filed: May 27, 2008

(65) Prior Publication Data

US 2008/0296786 A1 Dec. 4, 2008

Related U.S. Application Data

(60) Provisional application No. 60/935,715, filed on Aug. 28, 2007.

(30) Foreign Application Priority Data

Jun. 1, 2007 (DE) .................. 10 2007 025 904

(51) Int. Cl.
*C07C 31/30* (2006.01)
(52) U.S. Cl. .................................................. 568/851
(58) Field of Classification Search ................ None
See application file for complete search history.

(56) References Cited

U.S. PATENT DOCUMENTS

| 1,910,331 | A | 5/1933 | Halbig |
| 2,877,274 | A | 3/1959 | Kramis |
| 4,895,989 | A | 1/1990 | Sander |
| 6,759,560 | B2 | 7/2004 | Guth |
| 2002/0183566 | A1 | 12/2002 | Guth et al. |

FOREIGN PATENT DOCUMENTS

| DE | 968 903 | 4/1958 |
| EP | 0 299 577 | 1/1989 |
| EP | 1 242 345 A | 9/2002 |
| GB | 377 631 | 7/1932 |
| WO | WO 01/42178 A1 | 6/2001 |

OTHER PUBLICATIONS

European Search Report for European patent reference EP 08 15 4500, Sep. 2008.

*Primary Examiner*—Rosalynd Keys
(74) *Attorney, Agent, or Firm*—Law Office of: Michael A. Sanzo, LLC

(57) ABSTRACT

The invention relates to a process for preparing an alcoholic solution of an alkali metal alkoxide from alkali metal hydroxide and alcohol in a reaction column, the alcohol and the alkali metal hydroxide being conducted in countercurrent, which is characterized in that a reflux ratio of at least 0.05 is established in the reaction column.

18 Claims, 2 Drawing Sheets

US 7,847,133 B2

PROCESS FOR PREPARING ALKALI METAL ALKOXIDES

CROSS REFERENCE TO RELATED APPLICATIONS

The present application claims priority to German application no. 10 2007 025 904.4, filed on Jun. 1, 2007. The present application also claims priority to, and the benefit of, U.S. provisional application 60/935,715, filed on Aug. 28, 2007. The contents of these prior applications are hereby incorporated by reference in their entirety.

FIELD OF THE INVENTION

The present invention relates to a process for preparing alkali metal alkoxides from alkali metal hydroxides by means of reactive distillation.

BACKGROUND OF THE INVENTION

Alkali metal alkoxides are used as strong bases in the synthesis of numerous chemicals, for example in the preparation of active pharmaceutical or agrochemical ingredients. In addition, alkali metal alkoxides find use as catalysts in transesterification and amidation reactions.

Alkali metal alkoxides (MOR) are prepared by means of reactive distillation in a countercurrent distillation column from alkali metal hydroxides (MOH) and alcohols (ROH), the water of reaction formed being removed with the distillate according to the following reaction.

MOH+ROH ⇌ MOR+H$_2$O

Such a process principle is described, for example, in U.S. Pat. No. 2,877,274, in which aqueous alkali metal hydroxide solution and gaseous methanol are conducted in countercurrent in a rectification column. In basically unchanged form, this process is described again in EP 1 242 345.

Similar processes in which, however, an azeotroping agent, for example benzene, is used additionally are described in GB 377,631 and U.S. Pat. No. 1,910,331. The azeotroping agent serves to enable a separation of water and a water-soluble alcohol. In the two patents, the condensate is subjected to a phase separation in order to remove the water of reaction.

For instance, DE 96 89 03 also describes a process for continuously preparing alkali metal alkoxides, in which the water-alcohol mixture removed at the top is condensed and then subjected to a phase separation. In this case, the aqueous phase is discarded and the alcoholic phase is returned to the column at the top together with the fresh alcohol. A similar process is described by EP 0 299 577, in which the water is removed in the condensate with the aid of a membrane.

In practice, all processes have the disadvantage that, at the feed point of the alkali metal hydroxide solution—i.e. at the point in the column profile at which the concentration of the alkali metal hydroxide used is the greatest—the risk exists that solid precipitation occurs and the process has to be interrupted.

SUMMARY OF THE INVENTION

It was therefore an object of the present invention to provide a process for preparing an alcoholic solution of an alkali metal alkoxide which offers a stable continuous preparation process with high process reliability, in which commercial aqueous alkali metal hydroxide solutions can be used.

Surprisingly, a process has been found for preparing an alcoholic solution of an alkali metal alkoxide from alkali metal hydroxide and alcohol in a reaction column, the alcohol and the alkali metal hydroxide being conducted in counter-current, which is characterized in that a reflux ratio of at least 0.05 is established in the reaction column. In the case of a complete condensation, this means that at least 5% by weight of this condensate of the reaction column is returned to the reaction column in the form of a reflux at the top. As a result of the establishment of a reflux ratio in the reaction column, it is surprisingly possible to prevent solid precipitation below the feed point of the alkali metal hydroxide solution. Compared to the prior art processes, the process according to the invention has the advantage that the solubility limit of the alkali metal hydroxide at the feed point of the alkali metal hydroxide solution—at which the concentration of the alkali metal hydroxide used is the greatest—is not exceeded. The reflux ratio to be established in the process according to the invention is guided by the type of alkali metal alkoxide to be prepared and by the solubility of the corresponding alkali metal hydroxide in the mixture of water and the alcohol used which is established. In particular, this was surprising since the prior art processes are performed without reflux in the reaction column, or the water is withdrawn from the condensate by means of phase separation or membrane techniques before the now anhydrous reflux is recycled to the reaction column. The establishment of a reflux ratio ensures that, in the upper part of the reaction column, a sufficiently high water concentration is always present, such that solid precipitation is effectively prevented. A process is thus possible which is less sensitive to disruptions or variations, for example concentration variations in the feeds. In contrast to the prior art processes, in the process according to the invention, there is no removal of the water from the condensate before the reflux is recycled into the reaction column.

The invention thus provides a process for preparing an alcoholic solution of an alkali metal alkoxide from alkali metal hydroxide and alcohol in a reaction column, the alcohol and the alkali metal hydroxide being conducted in counter-current, which is characterized in that a reflux ratio of at least 0.05 is established in the reaction column.

BRIEF DESCRIPTION OF THE DRAWINGS

FIG. 2 shows a plant with a higher pressure in the reaction column 4 than in the rectification column 9. This plant differs from the plant in FIG. 1 in that the vapour stream 8 is conducted via a vapour compressor 20 into the reaction column 4. The vapour compressor 13 is dispensed with.

DETAILED DESCRIPTION OF THE INVENTION

Figure 1:
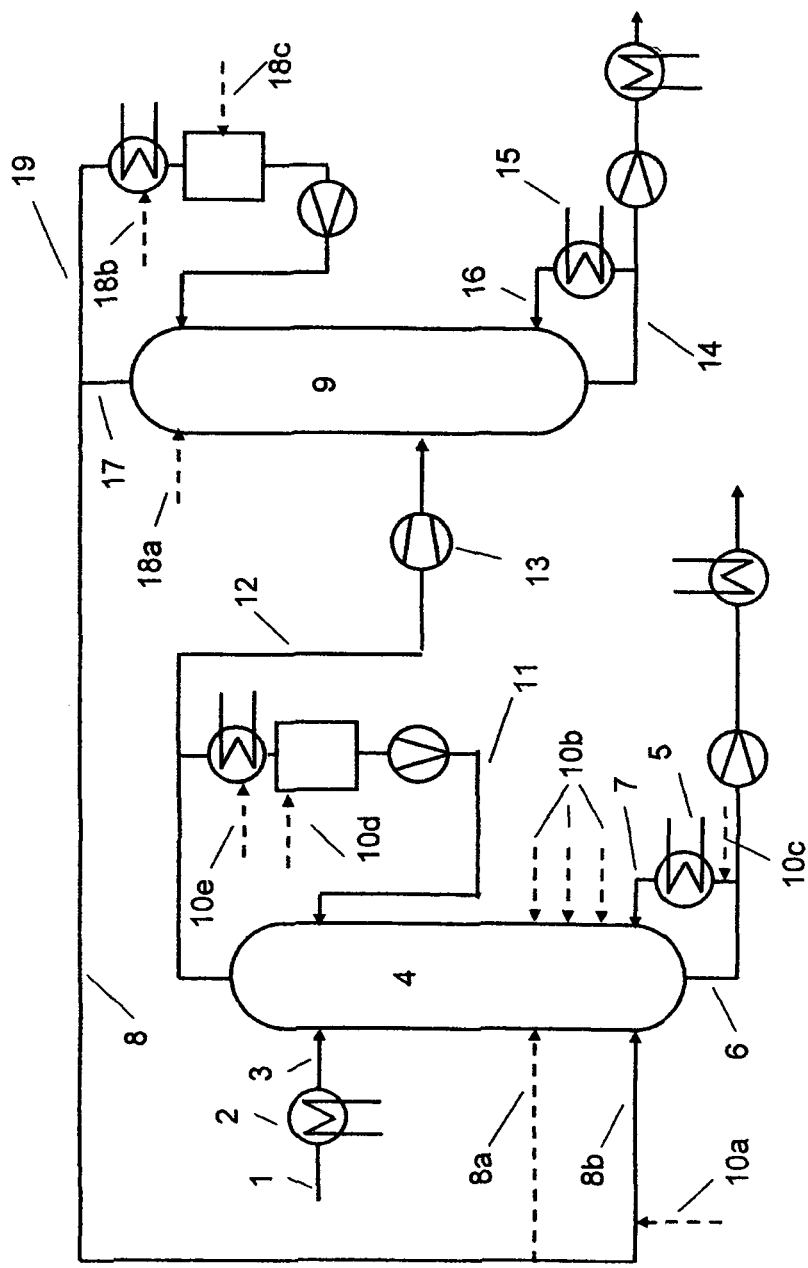
FIG. 1 shows a plant with a lower pressure in the reaction column 4 than in the rectification column 9. In this case, the alkali metal hydroxide solution is conducted via the pipeline 1 into a heat exchanger 2, in which it is heated to the temperature of the feed point, and is added via the pipeline 3 at the top of the column 4. The alkali metal alkoxide solution is withdrawn at the bottom of the column via the pipeline 6. At the bottom of the column is disposed an evaporator 5 with which the concentration of the alkali metal alkoxide solution is adjusted to the desired value. The vapours from the evaporator 5 are fed via the pipeline 7 at the lower end of the reaction column 4. The alcohol 8 recycled from the rectification column can be fed in at several points in the reaction column 4: 8a and 8b. In addition to the feeding of the recycled alcohol, fresh alcohol can also be fed via the feed lines 10a to 10e. At the top of the column, a portion of the vapours is condensed and can be recycled as reflux 11 back into the reaction column 4. The other portion of the vapours is conducted via a pipeline 12 and a vapour compressor 13 into the rectification column 9. At the bottom of this rectification column 9, water is withdrawn via the pipeline 14. The column is heated by means of the evaporator 15, which feeds the vapour stream via the pipeline 16 at the lower end of the rectification column 9. At the top of the rectification column 9, fresh alcohol can be applied to the top of the rectification column via the pipeline 18a. At the top of the rectification column, a portion of the vapours is condensed and recycled back into the rectification column 9 as reflux 19. The other portion of the vapours is transferred to the rectification column 4 via a pipeline 8. The fresh alcohol can also be added to the reflux of the rectification column at the feed points 18b and 18c.
Figure 2:
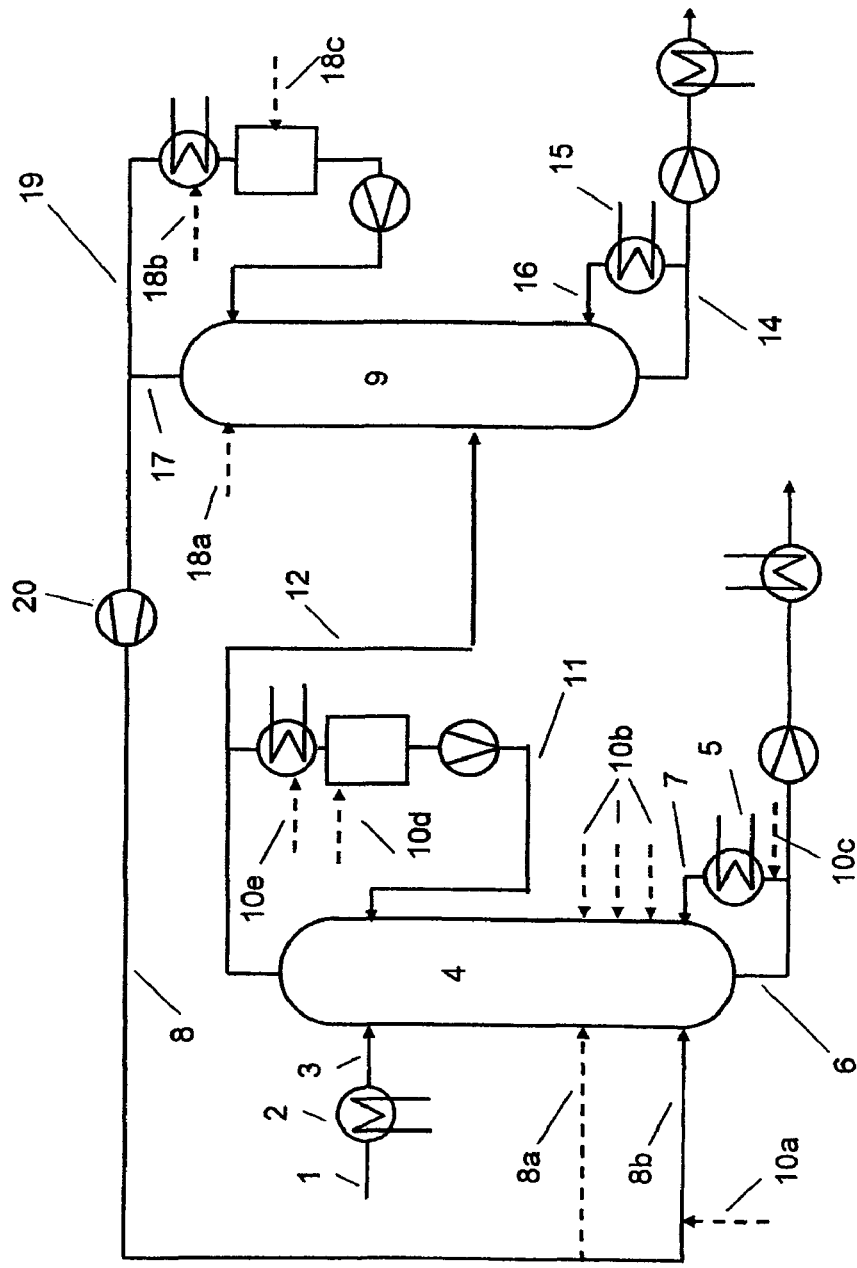

The reflux ratio in the process according to the invention is guided by the type of alkali metal alkoxide to be prepared and by the solubility of the alkali metal hydroxide used in the mixture of water and the alcohol used which is established. The vapours obtained in the reaction column are the alcohol with a small amount of water, at least 5% by weight of these vapours being condensed in these processes according to the invention and this condensate being recycled in the form of a reflux at the top of the reaction column, which corresponds to a reflux ratio of at least 0.05 in the reaction column. In the context of this invention, a reflux ratio is understood to mean the ratio of the mass flow (kg/h) which is recycled to the column in liquid form (reflux) and of the mass flow (kg/h) which is drawn off from the reaction column in liquid form (distillate) or gaseous form (vapour). In the reaction column, preference is given to establishing a reflux ratio of 0.11 to 0.34, more preferably of 0.14 to 0.27 and most preferably a reflux ratio of 0.17 to 0.24. Preference is thus given to recycling 10 to 25% by weight, more preferably 12 to 21% by weight and most preferably 15 to 19% by weight of the top product into the reaction column in the form of a reflux at the top thereof. In the process according to the invention, the water in the condensate and/or in the reflux of the reaction column is preferably not removed before the recycling as reflux into the reaction column. The establishment of a reflux ratio in the reaction column ensures that, in the upper part of the countercurrent distillation column, a sufficiently high water concentration is always present in the reaction mixture, such that solid precipitation can effectively be prevented.

The possible alkali metal hydroxides used in the process according to the invention may be sodium hydroxide, potassium hydroxide or lithium hydroxide; preference is given to using sodium hydroxide and potassium hydroxide. The alkali metal hydroxides may be used in the process according to the invention in the form of an aqueous solution, alcoholic solution or an aqueous solution which comprises the alcohol used as a further solvent.

The alkali metal hydroxides are used in the process according to the invention preferably as an aqueous solution; preference is given to using an aqueous solution having a content (by acidimetry) of alkali metal hydroxide of 15 to 55%, more preferably of 30 to 53% and more preferably of 45 to 52%.

In the process according to the invention, the alcohols used may be aliphatic alcohols having 1 to 5 carbon atoms, for example methanol, ethanol, n- or isopropanol, n-, sec-, iso- or tert-butanol, or isomers of pentanol, for example n-pentanol. In the process according to the invention, however, preference is given to using methanol or ethanol; particular preference is given to using methanol.

The alcohol used in the process according to the invention may serve both as the solvent and as a reactant. Moreover, the alcohol used can serve to strip water out of the liquid, such that it can be removed from the reaction chamber via the distillate. Therefore, in the process according to the invention, preference is given to using 15 to 45 times the amount, preferably 25 to 35 times the amount, of alcohol based on the weight of water in the feedstream of the alkali metal hydroxide.

It is advantageous to operate the reaction column at a pressure of 0.5 to 2 bar; preference is given to operating the reaction column at ambient pressure.

The alkali metal hydroxide solution is added in the process according to the invention preferably to the uppermost tray, or fed at the top of the reaction column. It is advantageous for the process according to the invention to feed the alkali metal hydroxide solution to the reaction column preferably with a temperature just below the boiling point of this solution. In the case of use of an aqueous sodium hydroxide solution, it is preferably heated to a temperature of 50 to 70° C. before supply into the reaction column, for example by means of a heat exchanger. The feed temperature of the alkali metal hydroxide solution should have the temperature of the tray at the feed point of the alkali metal hydroxide solution.

In the process according to the invention, the top product, i.e. vapour or distillate, which is not recycled as reflux to the reaction column, is separated in a further process step into water and alcohol—this can preferably be done in a rectification column, in which case the alcohol obtained by the separating stage can be fed to the rectification column as recycled alcohol.

It is thus possible to feed both recycled alcohol from the rectification column and fresh alcohol to the reaction column in the process according to the invention. Preference is given to feeding both recycled alcohol and fresh alcohol to the reaction column. Optionally, the fresh alcohol can be fed to the reaction column in a separate feed point or to the reaction column together with the recycled alcohol.

The recycled alcohol from the rectification column is preferably fed to the reaction column in gaseous form at least twenty trays below the feed point of the alkali metal hydroxide solution. The recycled alcohol is preferably metered in 1 to 10 trays, more preferably 1 to 6 trays, above the bottom, or directly into the bottom of the reaction column. Most preferably, the recycled alcohol is metered into the bottom of the reaction column.

The fresh alcohol can be used in the process according to the invention either as vapour or in liquid form. Preference is given to feeding the fresh alcohol into the bottom, into the evaporator or to a tray or to a plurality of trays which are 1 to 10, more preferably 1 to 6, trays above the bottom. In particular, the fresh alcohol is fed in the process according to the invention into the bottom or into the evaporator of the reaction column—preferably in gaseous form.

In a preferred embodiment of the process according to the invention, fresh alcohol is added into the upper part of the rectification column—especially together with the reflux of the rectification column. This embodiment of the process according to the invention is suitable especially for removing excess water from the methanol before the alcohol is conducted into the reaction column. Particular preference is given to adding the fresh alcohol to the condenser or to the condensate vessel on the rectification column; very particular preference is given to adding the fresh alcohol to the condenser on the rectification column.

In a particular embodiment of the process according to the invention, the fresh alcohol is added to the reflux of the reaction column; this can be done in the condenser or else into the condensate vessel on the reaction column.

The alcohol metered into the reaction column—both the recycled alcohol and the fresh alcohol—preferably has an average water content of not more than 1000 ppm (m/m), preferably not more than 500 ppm (m/m). It is particularly advantageous for the process according to the invention when the alcohol metered into the reaction column has an average water content of 200 to 450 ppm (m/m), preferably of 300 to 400 ppm (m/m).

The process according to the invention can be operated either continuously or semicontinuously. In the case of semicontinuous operation, the alcohol, preferably methanol, is initially charged in the evaporator of the reaction column, the alcohol is metered in during operation to the column bottom in liquid form, or in gaseous form at the lowermost or one of the lower trays of the column, and an alkali metal hydroxide solution is metered in at the top of the reaction column.

However, preference is given to operating the process according to the invention continuously. In this case, alkali metal hydroxide solution is preferably metered in at the top of the reaction column, while gaseous alcohol is metered into the bottom of the reaction column.

The reaction column of the process according to the invention preferably has column trays of the bubble-cap tray type, selected from bubble-cap trays, tunnel-cap trays, Thormann trays or cross-slit bubble-cap trays, as internals. In a further embodiment of the process according to the invention, the reaction column may also have sieve trays or valve trays, structured or unstructured packings or random packings.

The product stream in the process according to the invention is advantageously withdrawn at the column bottom or evaporator and consists of an alcoholic solution of the desired alkali metal alkoxide, for example as a 30% solution. This product stream may optionally have small amounts of water and/or unreacted alkali metal hydroxide.

The distillate not recycled into the reaction column is preferably separated in a separate step in the process according to the invention, and the alcohol freed of water can thus be recycled into the reaction column. Preferred processes for this workup of the alcohol are distillation, drying by means of membrane processes or drying by means of a molecular sieve, as known to those skilled in the art. Preference is given to performing this workup of the alcohol in the process according to the invention by means of distillation.

In a particularly preferred embodiment of the process according to the invention, the top product which has been withdrawn at the top of the reaction column and has not been recycled into the reaction column as reflux is worked up in a rectification column at a higher pressure than in the reaction column. It is advantageous for the process according to the invention to conduct this portion of the top product of the reaction column into the rectification column via a vapour compressor. The water is discharged from the system via the bottom effluent of the rectification column. The distillate obtained at the top of the rectification column can in turn be recycled to the reaction column.

It is likewise possible to perform the reaction at higher pressure than the rectification and to recycle the top product of the rectification column into the reaction column by means of a vapour compressor.

The rectification of the mixture of alcohol and water can be effected in the process according to the invention according to known process steps, as described, for example, in "Distillation: Principles and Practices" (Johan G. Stichlmair, James R. Fair; Wiley-VCH).

In the case of use of methanol as the alcohol in the process according to the invention, the distillate of the reaction column is preferably worked up in a rectification column. Suitable internals here are all known internals, both trays and structured packings and random packings. The methanol is obtained here as low-boiling distillate at the top of the rectification column, and the water can be withdrawn at the bottom of the rectification column. The reflux ratio here is preferably greater than 0.5 and is preferably 0.8 to 1.5. The pressure in the rectification column can be selected at either a lower or higher level than in the reaction column. The temperature is established correspondingly. The methanol/water feed is introduced into the lower half of the rectification column, preferably from the 2nd to 15th tray above the evaporator. In this preferred embodiment of the process according to the invention, fresh alcohol is added to the upper part of the rectification column—especially together with the reflux of the rectification column—in order to remove excess water from the methanol before the alcohol is recycled into the rectification column. Particular preference is given to adding the fresh alcohol to the condenser or to the condensate vessel on the rectification column; very particular preference is given to adding the fresh alcohol to the condenser on the rectification column.

In the case of use of ethanol, n- or isopropanol, n-, sec-, iso- or tert-butanol, or in the case of the isomers of pentanol, preference is likewise given to selecting distillative, optionally multistage processes for the workup of the alcohol in the process according to the invention, in which the azeotropes or heteroazeotropes can be separated by means of techniques known to those skilled in the art. The assistants used may be prior art azeotroping agents which are capable of forming heteroazeotropes with the alcohol. However, it is also possible to use adsorbents, for example zeolites, for this purpose.

The examples which follow are intended to illustrate the process according to the invention for preparing alkali metal alkoxides in detail, without any intention that the invention be restricted to this embodiment.

EXAMPLES

1. Continuous Process

Example 1.1 (Inventive)

At the top of a 9 metre-high reaction column equipped with 40 bubble-cap trays and having an internal diameter of 80 mm, 0.53 kg/h of a 50% aqueous sodium hydroxide solution is heated to about 60° C. and fed to the uppermost tray. The reaction column is equipped with an electrical compensation heater which comprises 10 trays in each case in order to minimize heat losses to the environment. The temperature of the compensation heater is regulated in each case to the internal temperature of the middle tray of the particular section. 12% by weight of the condensate of the reaction column are recycled to the reaction column in the form of a reflux, i.e. a reflux ratio of 0.14 is established in order to reduce the proportion of dissolved solid in the liquid phase. In addition, it is operated at ambient pressure. Between the evaporator and the lowermost tray of this reaction column, 8.88 kg/h of vaporous methanol with a water content of 400 ppm (m/m) and a temperature of about 70° C. are passed into the reaction column, which ascends in countercurrent to the liquid phase in the column.

A product stream of 1.16 kg/h which consists of a 30% sodium methoxide solution in methanol and whose concentration of water and unreacted sodium hydroxide—calculated as sodium hydroxide—is a total of 0.18% by weight is withdrawn from the evaporator of the reaction column. The temperature at the top of the column is 75° C. An amount of condensate of 8.25 kg/h, which consists of pure methanol with a 5% water content, is obtained there. About 1 kg/h of the condensate is recycled as reflux into the column.

The total alkalinity, i.e. the concentration of sodium hydroxide and sodium methoxide in the liquid phase, is reduced to below 20% by weight by this measure, i.e. the liquid phase is diluted and the concentrations of sodium hydroxide and sodium methoxide are significantly below the particular solubility limit. This is true especially of sodium hydroxide, since the water recycled significantly increases the water content in the liquid phase. The sodium hydroxide thus remains in solution. Therefore, no solid precipitation can be observed in the reaction column.

Example 1.2 (Not Inventive)

At the top of a 9 metre-high reaction column equipped with 40 bubble-cap trays and having an internal diameter of 80 mm, 0.55 kg/h of a 50% aqueous sodium hydroxide solution is heated to about 60° C. and fed to the uppermost tray. The reaction column is equipped with an electrical compensation heater which comprises 10 trays in each case in order to minimize heat losses to the environment. The temperature of the compensation heater is regulated in each case to the internal temperature of the middle tray of the particular section. The column is operated without reflux, and is operated at ambient pressure. Between the evaporator and the lowermost tray of this reaction column, 8.74 kg/h of vaporous methanol having a water content of 400 ppm (m/m) and a temperature of about 70° C. are passed into the reaction column, which ascends in countercurrent to the liquid phase in the column.

A product stream of 1.27 kg/h which consists of a 30% sodium methoxide solution in methanol and whose concentration of water and unreacted sodium hydroxide—calculated as sodium hydroxide—is a total of 0.15% by weight is withdrawn from the evaporator of the reaction column. The temperature at the top of the column is 75° C. An amount of condensate of 8.01 kg/h is obtained there, which consists of pure methanol with a 5% water content.

The total alkalinity, i.e the concentration of sodium hydroxide and sodium methoxide in the liquid phase, is significantly above 30% by weight. The sodium hydroxide concentration in the upper part of the column is significantly higher and the water concentration is significantly lower than in Example 1.1. Solid precipitation is observed on the upper trays of the column.

2. Semicontinuous Process

A laboratory distillation apparatus is constructed as follows: A multineck flask is equipped with two column sections, which are connected via an intermediate piece for incorporation of a thermometer, and with a stirrer, thermometer and a metering means at the bottom. The column sections used may, as desired, be tray columns or packed columns; it is likewise possible to use different column types above and below the temperature measurement point. The column is equipped with a reflux divider. To check the solid formation, preference is given to using a bubble-cap tray column made from glass. The top of the distillation column is equipped with a cooler, reflux divider and a metering means at the top. The incoming streams in the top or at the bottom can be heated if desired.

Example 2.1 (Inventive)

The reaction column selected has the following construction: Below the temperature measurement point, a column section with steel wool packing (20 cm) and, above it, a bubble-cap tray column with 9 trays are used. The two columns have a diameter of 29 mm. The apparatus is charged with 720 g of methanol, which is heated to boiling. The reflux divider is adjusted to a reflux ratio of 0.16, such that approx. 300 g of distillate per h are obtained. At the top of the reaction column, a 50% aqueous sodium hydroxide solution is metered in at a rate of 13 g/h. 290 g/h of methanol are metered in via the metering means at the bottom. No solid precipitation is observed.

After 6 hours, the metered addition of the sodium hydroxide solution at the top is ended. For a further 30 minutes, methanol is metered in at the bottom of the column and distillation is continued with the same condensate removal. After 6.5 hours, 697 g of a 10% sodium methoxide solution in methanol are obtained, which has a concentration of water and unreacted sodium hydroxide—calculated as sodium hydroxide—of 0.75% by weight in total.

Example 2.2 (not inventive)

The reaction column used is the apparatus described under Example 2.1. The apparatus is charged with 720 g of methanol, which is heated to boiling so as to obtain approx. 460 g of distillate per h. At the top of the reaction column, a 50% aqueous sodium hydroxide solution is metered in at a rate of 20 g/h. The apparatus is operated without reflux. After approx. 1 hour, significant solid precipitation is observed on the uppermost 3 trays of the bubble-cap tray column.

After 6 hours, the metered addition of the sodium hydroxide solution at the top is ended. For a further 30 minutes, methanol is metered in at the bottom of the column and distillation is continued with the same condensate removal. After 6.5 hours, 582 g of a 13% sodium methoxide solution in methanol are obtained, which has a concentration of water and unreacted sodium hydroxide—calculated as sodium hydroxide—of 0.57% by weight in total.

Example 2.3 (Inventive)

The reaction column used is the apparatus described under Example 2.1. The apparatus is charged with 720 g of methanol, which is heated to boiling. The reflux divider is adjusted to a reflux ratio of 0.16, such that approx. 460 g of distillate per h are obtained. At the top of the reaction column, a 50% aqueous sodium hydroxide solution is metered in at a rate of 20 g/h. No solid precipitation is observed.

After 6 hours, the metered addition of the sodium hydroxide solution at the top is ended. For a further 30 minutes, methanol is metered in at the bottom of the column and distillation is continued with the same condensate removal. After 6.5 hours, 814 g of an 11% sodium methoxide solution in methanol are obtained, which has a concentration of water and unreacted sodium hydroxide—calculated as sodium hydroxide—of 0.57% by weight in total.

Analysis Method:

The concentration of water and unreacted alkali metal hydroxide is determined by means of a modified Karl-Fischer titration, as is typically used for determining water contents.

This detects water and alkali metal hydroxide together as a cumulative parameter. The corresponding content is reported in % by weight—calculated as alkali metal hydroxide.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A process for preparing an alcoholic solution of an alkali metal alkoxide, comprising:
    a) reacting an alkali metal hydroxide with an alcohol in a reaction column, wherein:
        i) said an alkali metal hydroxide and said alcohol flow in countercurrent to one another in said reaction column;
        ii) alcohol vapors are withdrawn from said reaction column and divided into a reflux that is fed back into said reaction column and a distillate, with the ratio of reflux to distillate (reflux ratio) of at least 0.05; and
    b) recovering said alcoholic solution of an alkali metal alkoxide from said reaction column, wherein water is not removed from the alcohol vapors being refluxed back into said reaction column.

2. The process of claim 1, wherein said alkali metal hydroxide is in the form of an aqueous solution, alcoholic solution or an aqueous solution comprising an alcohol.

3. The process of claim 1, wherein a solution of said alkali metal hydroxide is fed into the top of said reaction column.

4. The process of claim 1, wherein said alcohol is fed into said reaction column in gaseous form at least twenty trays below the feed point of the solution of the alkali metal hydroxide.

5. The process of claim 1, wherein said distillate which is not recycled to the reaction column is separated in a further process step into water and said alcohol, and the alcohol recovered in this further process step is recycled to the reaction column.

6. The process of claim 5, wherein said alcohol is methanol.

7. The process of claim 5, wherein the total alcohol metered into the reaction column has an average water content of 200 to 450 ppm (m/m), said total alcohol comprising both alcohol recovered in said further process step and any fresh alcohol added to said reaction column.

8. The process of claim 5, wherein said distillate is separated into water and alcohol using a rectification column that is connected to said reaction column.

9. The process of claim 8, wherein said rectification column has a higher pressure than said reaction column.

10. The process of claim 9, wherein said distillate which is not recycled to the reaction column is conducted into said rectification column via a vapor compressor.

11. The process of claim 8, wherein said reaction column has a higher pressure than said rectification column.

12. The process of claim 11, wherein, after the removal of water, said alcohol is recycled back to said reaction column via a vapour compressor.

13. The process of claim 8, wherein fresh alcohol is added to a condenser or condensate vessel on the rectification column.

14. A process for preparing an alcoholic solution of an alkali metal alkoxide, comprising reacting an alkali metal hydroxide and an alcohol in a reaction column, wherein:
    a) said alkali metal hydroxide is fed into said reaction column as a solution at a first site and said alcohol is fed into said reaction column as gas at a second site below said first site, so that said alcohol and said alkali metal hydroxide flow in countercurrent in said reaction column;
    b) alcohol vapors are withdrawn from said reaction column at a site above said second site and divided into a reflux that is fed back into said reaction column and a distillate that is not fed back into said reaction column, with the reflux ratio of said reflux to said distillate being at least 0.05 wherein water is not removed from the alcohol vapors being refluxed into said reaction column.

15. The process of claim 14, wherein said second site is at least twenty trays below said first site.

16. The process of claim 14, wherein said alcohol is methanol.

17. The process of claim 16, wherein said alkali metal hydroxide consists of sodium hydroxide or potassium hydroxide.

18. The process of claim 17, wherein said distillate which is not recycled to the reaction column is separated into water and said alcohol on a rectification column and the alcohol recovered after this separation is recycled to the reaction column.

* * * * *